US007833188B2

(12) United States Patent
Gerber

(10) Patent No.: US 7,833,188 B2
(45) Date of Patent: Nov. 16, 2010

(54) ASPIRATION PREVENTION MECHANISM

(76) Inventor: Allen Gerber, 42 Nutmeg Rd., High Falls, NY (US) 12440

( * ) Notice: Subject to any disclaimer, the term of this patent is extended or adjusted under 35 U.S.C. 154(b) by 619 days.

(21) Appl. No.: 11/545,382

(22) Filed: Oct. 10, 2006

(65) Prior Publication Data

US 2008/0171963 A1 Jul. 17, 2008

(51) Int. Cl.
*A61M 31/00* (2006.01)
*A47B 7/02* (2006.01)

(52) U.S. Cl. ............................... 604/67; 604/66; 5/610; 5/618

(58) Field of Classification Search ............. 604/65–67, 604/910; 5/600–624, 940; 417/18; 600/584, 600/587, 593–595; 200/61.45 R, DIG. 2
See application file for complete search history.

(56) References Cited

U.S. PATENT DOCUMENTS

| | | | | |
|---|---|---|---|---|
| 3,860,000 | A * | 1/1975 | Wootten et al. | 604/28 |
| 4,348,562 | A | 9/1982 | Florin | |
| 4,547,972 | A | 10/1985 | Heidel et al. | |
| 4,869,266 | A * | 9/1989 | Taylor et al. | 600/587 |
| 5,199,122 | A | 4/1993 | Styblo | |
| 5,611,096 | A * | 3/1997 | Bartlett et al. | 5/617 |
| 5,941,836 | A | 8/1999 | Friedman | |
| 6,447,472 | B1 * | 9/2002 | Moss | 604/27 |
| 6,537,244 | B2 * | 3/2003 | Paukovits et al. | 604/65 |
| 6,742,993 | B2 | 6/2004 | Savard et al. | |
| 7,017,211 | B2 | 3/2006 | Krywiczanin et al. | |
| 7,052,474 | B2 | 5/2006 | Castell et al. | |
| 6,892,405 | B1 | 5/2007 | Dimitriu et al. | |
| 2001/0041861 | A1 | 11/2001 | Gobel | |
| 2006/0021240 | A1 * | 2/2006 | Horgan | 33/366.11 |
| 2007/0268480 | A1 * | 11/2007 | Kaye | 356/138 |

OTHER PUBLICATIONS

Peggy Guenter, et al. Enteral Feeding Misconnections: A Consortium Position Statement, May 2008, pp. 285-292, vol. 34, No. 5, The Joint Commission Journal on Quality.

Marianne Opilla, Aspiration Risk and Enteral Feeding: A Clinical Approach, Apr. 2003,pp. 89-90,92-94,96, Series #4, Practical Gastroenterology.

* cited by examiner

*Primary Examiner*—Nicholas D Lucchesi
*Assistant Examiner*—Nathan R Price
(74) *Attorney, Agent, or Firm*—Lawrence D. Cutter, Esq.

(57) ABSTRACT

A patient angle sensor is employed in conjunction with gastric feeding devices to shut off or to reverse the flow of fluid in the tube when the angle of a bed ridden patient becomes sufficient to allow gastric juices to percolate up through the esophagus and into the patient's lungs. In this way incidents of aspirational pneumonia in hospitalized patients is significantly reduced or eliminated.

12 Claims, 3 Drawing Sheets

ASPIRATION PREVENTION MECHANISM

TECHNICAL FIELD

The present invention is generally directed to the medical field as it relates to patient care, particularly in a hospital, nursing home or other institutional setting. More particularly, the present invention relates in general to systems and methods for preventing aspiration of stomach contents by bed ridden patients connected to feeding tubes.

BACKGROUND OF THE INVENTION

It is well known that millions of people around the world are fed through gastric feeding tubes once they can no longer feed themselves. The most common version of this practice occurs in the use of nasogastric feeding tubes. Other gastric feeding practices include the surgical insertion of a feeding tube directly into the stomach through the abdominal wall. The present invention is employable in all of these situations in which gastric feeding is provided.

While the use of gastric feeding mechanisms is not only a common but a life preserving procedure, complications can arise. In particular, one of these complications is aspiration pneumonia. This condition, which can be life threatening, particularly in older patients or in patients with weakened immune systems, can occur via several mechanisms. A common one of these mechanisms is one in which the patient slides down in bed to a low angle sufficient to allow gastric fluids to ascend the esophagus and be inhaled into the lungs. Typically, this angle is about 30°. When the patient angle in the bed reaches this point, the stomach contents are able to percolate up through the esophagus and down into the lungs. The fact that this is a significant problem in patient care is reflected in the fact that in many states the occurrences of aspirational pneumonia are reportable incidents to state oversight authorities.

It is noted that, while the present invention is principally directed to the problems associated with gastric feeding tubes, nonetheless, it is equally applicable to those situations in which substances other than nourishment are being provided through such a tube.

SUMMARY OF THE INVENTION

Accordingly, in order to solve these problems, there is provided a mechanical or electronic device that senses when a patient slides down below a predetermined angle. The device may also operate to turn off the pump in order to prevent further fluid from entering the stomach and hence the esophagus. Additionally, not only does the device shut off the pump, but it includes an optional but desired modality in which it also actually withdraws residual liquid from the tube.

The sensing of patient position below a certain angle may also be used to alert the attending medical staff that a patient is in an undesirable position. Additionally, the detection of an undesirable patient angle may also be employed to automatically raise the head and/or foot portion of an adjustable bed so as to prevent further downward sliding.

Accordingly, it is an object of the present invention to reduce and/or eliminate the problem of aspiration in patients connected to gastric tubes.

It is also an object of the present invention to reduce and/or eliminate the problem of exposing portions of the esophagus to gastric fluids.

It is a still further object of the present invention to provide medical staff with an indication of undesired patient movement.

It is yet another object of the present invention to provide a feedback mechanism for raising the foot portion of a patients bed to prevent further sliding.

Lastly, but not limited hereto, it is an object of the present invention to

Additional features and advantages are realized through the techniques of the present invention. Other embodiments and aspects of the invention are described in detail herein and are considered a part of the claimed invention.

The recitation herein of a list of desirable objects which are met by various embodiments of the present invention is not meant to imply or suggest that any or all of these objects are present as essential features, either individually or collectively, in the most general embodiment of the present invention or in any of its more specific embodiments.

BRIEF DESCRIPTION OF THE DRAWINGS

The subject matter which is regarded as the invention is particularly pointed out and distinctly claimed in the concluding portion of the specification. The invention, however, both as to organization and method of practice, together with the further objects and advantages thereof, may best be understood by reference to the following description taken in connection with the accompanying drawings in which:

DETAILED DESCRIPTION

Figure 1:
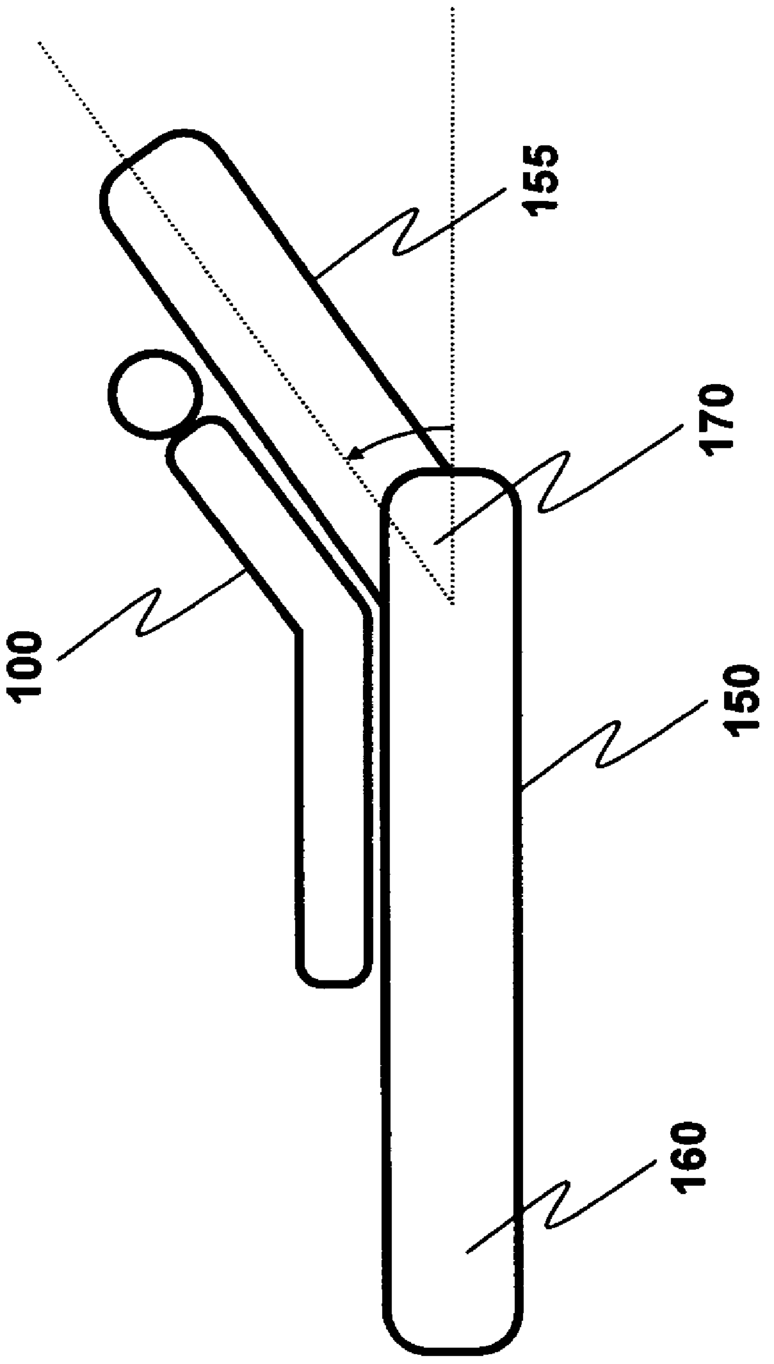
FIG. 1 is a side elevation view indicating the relative positions of a patient and a reclinable bed, and particularly indicating the angle of the bed.

FIG. 1 illustrates the environment in which the present invention is employed. In particular, there is shown patient 100 positioned in a reclining position on bed 150 which includes movable head portion 155 and which may also include a likewise movable foot portion 160 which is employed either for patient comfort or for elevation of the lower extremities. It is also seen the patient is reclining at angle 170 with respect to the horizontal. Reference to the horizontal is employed herein for measurement and determination of improper angle since the "horizontal" is really determined by gravity and it is gravity that is the principal driver of gastric fluid into the esophagus and beyond.

It is noted herein that the angle shown in FIG. 1 is the angle of the adjustable head portion of the bed with respect to the horizontal portion of the bed. Even though the illustration suggests it, FIG. 1 does not reflect the fact that the position of a patient who has slid down in the bed. It should also be noted that the beds of concern herein may also be equipped with adjustable foot portion 160 as well. In fact, if it is detected that patient 100 is sliding down in the bed, the adjustable foot portion of the bed may be raised to prevent further sliding. This is an optional feature of the present invention.

Figure 2:
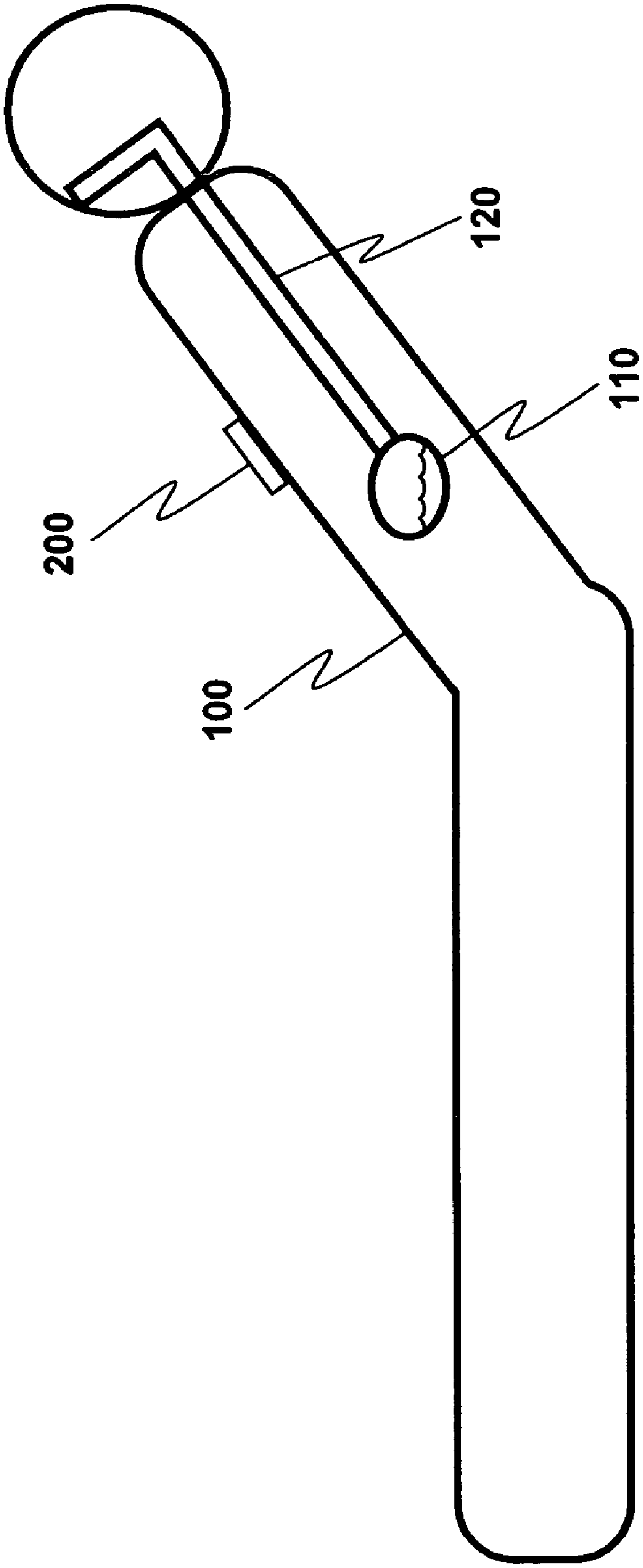
FIG. 2 is a stylized, side elevation view of a patient showing the stomach and esophagus for a patient reclining at the angle shown in FIG. 1, as well as showing the placement of an angle sensor.

FIG. 2 provides a greater detail of the situation being considered with respect to patient 100 and the specific problem that is solved. Basic human anatomy teaches that stomach 110 is connected to esophagus 120. It is easily seen that if the patient's angle is low, that is, if the patient is closer to a horizontal position, stomach, contents can enter esophagus 120 simply by gravity flow. The problems associated with this flow are discussed above, but, needless to say, it is not a desirable situation.

Additionally, FIG. 2 illustrates the placement of sensor 200. Sensor 200 is preferably placed on the chest of patient 200. It is affixed to the patient or to the patient's clothing by any convenient means. For short term use adhesive material on one side of sensor 200 holds it in place. For use with clothing or gowns, a wider range of options is available for affixing the sensor, including pins, elastic bands and Velcro™. Sensor 200 comprises any convenient mechanism for sensing angle. At its simplest it comprises a mercury filled insulative container with electrical contacts being closed when it contact with the mercury. The interior shape of the container is such that the mercury becomes in contact with the contacts at a predetermined angle. The sensor may also include adjustable exterior flaps to provide a selectable angle. It is noted, however, that there is a wide range of sensors and sensor technology which may be employed. For example, one could employ a ball or other sliding or rolling interior object which either makes electrical contact or which is of sufficient weight to cause switch contacts to close. Additionally, the interior moving object may be employed to interrupt light falling on a photocell. Magnetic or other optical sensors may be employed as well. In fact, any device which implements the generation of an electrical or even electromagnetic signal based on dependence on an angle with respect to feeding tube flow is employable. As indicated, the sensor may even comprise a wireless device which transmits an activation signal to pump control 220. More sophisticated sensors 200 which actually provide a signal indicative of the actual angle, as opposed to the angle merely exceeding a threshold value are also employed in the present invention. With a more sophisticated indication of angle being provided, it is then possible to provide an early warning indication of a patient sliding downward. I such cases, the alarm to patient or staff is variable in intensity depending on the angular degree sensed.

Figure 3:
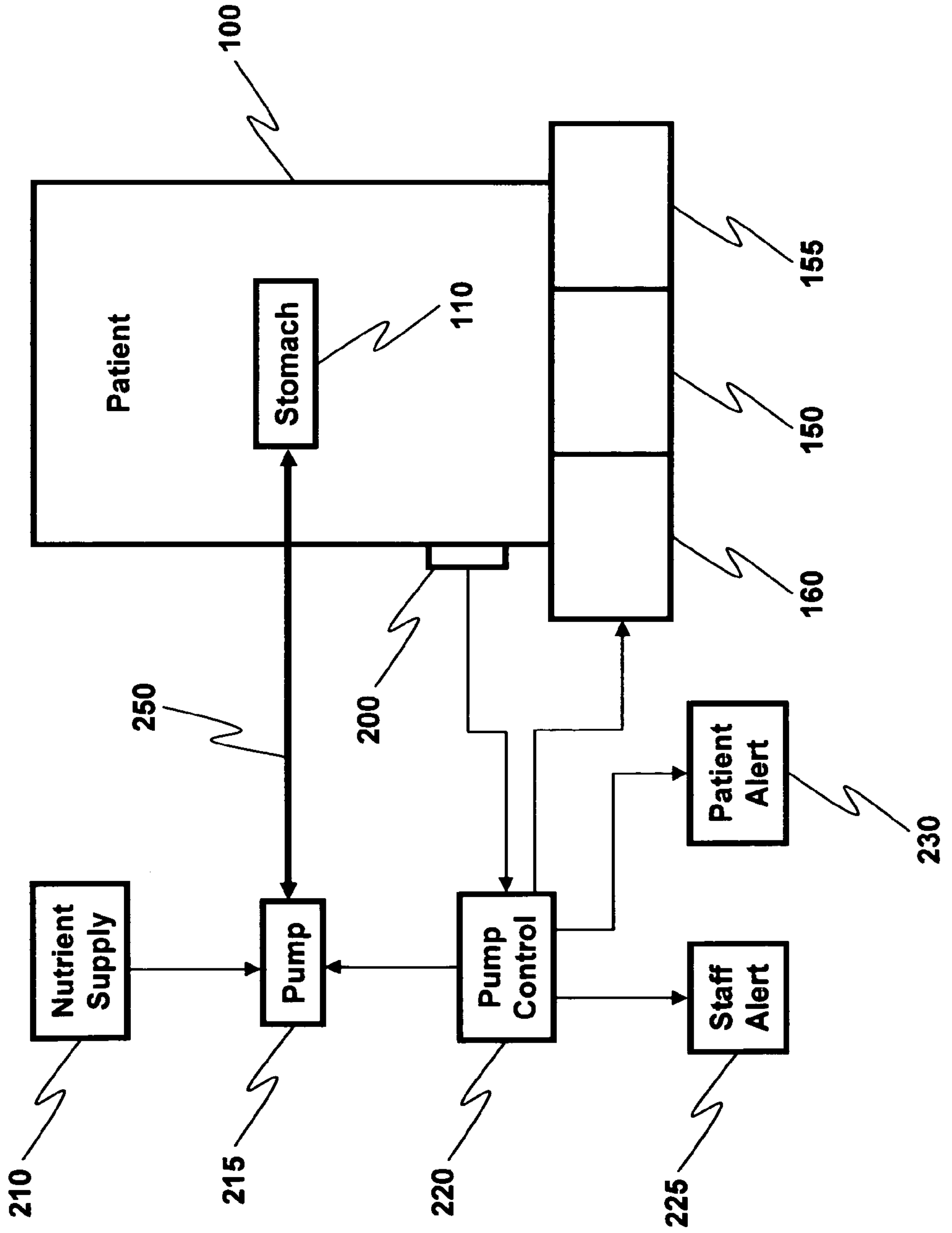
FIG. 3 is a block diagram illustrating the system and method of the present invention.

The solution to the aspiration problem is shown in greater detail in FIG. 3. In particular, sensor 200, which is affixed to patient 100, sends a signal to pump control 220 which, in normal operation, sends nutrient materials from supply 210 to stomach 110 of patient 100. If patient 100 slides down in bed 150 to an undesired, predetermined angle, sensor 200 signals pump control 220 to shut off the supply of nutrient or other material to stomach 110. Additionally, the system is provided with an optional feature in which gastric fluid is actually pulled back into gastric tube 250. In this regard, note the two directions indicated for tube 250.

It is also seen that the signal from sensor 200 is also capable of providing an audible or visual signal 225 to hospital staff members to alert them that patient 100 has slid down into bed 150 to an undesirable and possibly unsafe position. Pump control 220 may also be used to supply an audible, visual or vibratory signal 230 to patient 100 as a mechanism for immediate correction by the patient himself or herself, if possible. This same signal from sensor 200 may also be used to control bed 150. In particular, in conjunction with a bed control unit (not shown), sensor 200 is also seen to be capable of providing an actuation signal to cause foot portion 160 of bed 150 to raise so as to forestall further sliding.

In the discussion above, it is assumed that nutrients are provided through a gastric tube via a pump which acts as a positive control element in the system. However, it is noted that it is also possible that nutrient supply 210 may be positioned above the patient so that it is supplied by gravitational action. In this case, the role of "pump" 220 is less "active" in that it operates not so much as a pump but as a valve to control the rate of flow. In such an arrangement the optional feature of pump reversal is not available. However, apart from this drawback, the present invention is equally capable of operating with gravity flow systems.

Pump control 220 is provided by any convenient mechanism. Application specific integrated circuit (ASIC) chips may be employed, off-the shelf control components may be used or pump control 220 may be implemented via any standard microprocessor or microcontroller.

While the invention has been described in detail herein in accordance with certain preferred embodiments thereof, many modifications and changes therein may be effected by those skilled in the art. Accordingly, it is intended by the appended claims to cover all such modifications and changes as fall within the true spirit and scope of the invention.

What is claimed is:

1. A device to prevent aspiration of gastric fluids in a patient, said device comprising:

a gastric tube which provides fluid to said patient's stomach cavity;

an angle sensor, said angle sensor providing an electrical signal indicative of the angle sensor's being angularly positioned beyond a threshold angle, wherein angular position of said angle sensor corresponds to angular position of said patient; and an electrical control circuit which receives said electrical signal from said angle sensor and which stops flow in said gastric tube when said electrical signal from said angle sensor indicates positioning of said angle sensor beyond said threshold angle.

2. The device of claim 1 in which said electrical control circuit is also capable of reversing flow in said gastric tube.

3. The device of claim 1 in which said gastric tube is a gastric feeding tube.

4. The device of claim 1 in which said angle sensor includes means for affixation to said patient.

5. The device of claim 1 in which said electrical control circuit also actuates an alarm to alert attending staff.

6. The device of claim 1 in which said electrical control circuit also actuates an alarm to alert said patient.

7. The device of claim 1 in which said angular threshold is adjustable.

8. The device of claim 1 in which said electrical control circuit also operates to raise a head portion of said patient's bed.

9. The device of claim 1 in which said electrical control circuit also operates to raise a foot portion of said patient's bed.

10. The device of claim 1 in which said angle sensor includes a wireless transmitter to supply said electrical signal to said electrical control circuit which includes a receiver for said signal.

11. A device to prevent aspiration of gastric fluids in a patient, said device comprising:

a gastric tube which provides fluid to said patient's stomach cavity;

an angle sensor affixable to said patient providing an electrical signal indicative of angular position of said angle sensor, wherein the angular position of said angle sensor corresponds to angular position of the patient; and an electrical control circuit which receives said electrical signal from said angle sensor and which stops flow in said gastric tube, as a function of said angular position as indicated by said electrical signal.

12. The device of claim 1 in which said angle sensor is affixable to a patient.

* * * * *